United States Patent [19]

Flitsch et al.

[11] Patent Number: 5,874,548
[45] Date of Patent: Feb. 23, 1999

[54] REGIOSELECTIVE SULFATION

[75] Inventors: Sabine Flitsch; Benedicte Guilbert, both of Oxford, Great Britain

[73] Assignee: Genzyme Corporation, Framingham, Mass.

[21] Appl. No.: 765,930

[22] PCT Filed: Jul. 27, 1995

[86] PCT No.: PCT/EP95/03034

§ 371 Date: May 16, 1997

§ 102(e) Date: May 16, 1997

[87] PCT Pub. No.: WO96/03413

PCT Pub. Date: Feb. 8, 1996

[30] Foreign Application Priority Data

Jul. 27, 1994 [GB] United Kingdom ................ 9415169
Nov. 4, 1994 [GB] United Kingdom ................ 9422304

[51] Int. Cl.$^6$ ................ C07H 1/00; C07H 5/10; C07H 5/04
[52] U.S. Cl. ................ 536/1.11; 536/122; 536/123.13; 536/124; 536/55.2
[58] Field of Search ................ 536/1.11, 124, 536/123.13, 122, 55.2

[56] References Cited

FOREIGN PATENT DOCUMENTS 908770119   7/1990   European Pat. Off. .
WO 93/20226 10/1993  WIPO .
WO 94/00596 1/1994   WIPO .

OTHER PUBLICATIONS

Alais, J. et al., "Regioselective Mono–o–alkylation of Disaccharide Glycosides Through Their Dibutylstannylene Complexes", *Tetrahedron Letters*, 24:23, 2383–2386 (1983).

Alais, J. et al., "Synthesis of O–β–D–Galactopyranosyl–(1→4)–O–2–acetamido–2–deoxy–β–D–glucopyranosyl–(1→3)–D–mannose, a Postulated Trisaccharide of Human Erythrocyte Membrane Sialoglycoprotein", *J.C.S. Perikins*, 377–381 (1981).

Chandrasekaran, R.K. et al., "Ovarian Cancer α–1,3–L–Fucosyltransferase" *J. of Biological Chemistry*, 267:33, 23806–23814 (1992).

Closs, G.L. et al., "Enzyme–Catalyzed Synthesis of N–Acetyllactosamine with in Situ Regeneration of Uridine 5'–Diphosphate Glucose and Uridine 5'–Disphosphate Galactose", *J. Org. Chem.,,* 47, 5416–5418 (1982).

David, S. et al., "Regioselective Manipulation of Hydroxyl Groups via Organotin Derivatives", *Tetrahedron*, 41:4, 643–663 (1985).

Davis, N.J. et al., "Chemical Synthesis of Disaccharides which are Partial Structures of the Glycosaminoglycan Heparan Sulfate", *J. Chem. Soc. Perkins Transactions* 1, 359–368 (1994).

Davis, N.J. et al., "Synthesis of Sulfated Oligosaccharides", *Davis' Thesis—Oxford Univ.,* (1994).

Fujita, K. et al., "Selective Preparation of Hexakis(6–O–Arenesulfonyl)–α–Cyclodextrin", *Tetrahedron Letters*, 33:38, 5519–5520 (1992).

Glen, A. et al., "The Regioselective Tert–butyldimethylsilylation of the 6'–hydroxyl Group of Lactose Derivatives via their Dibutylstannylene Acetals" *Carbohydrate Research*, 248,. 365–369 (1993).

Guilbert, B. et al., "A Short Chemo–Enzymic Route to Glycosphingolipids Using Soluble Glycosyl Transferases", *J. Chem. Soc. Perkin Trans.* 1, 1181–1186 (1994).

Guilbert, B. et al., "Regioselective Sulfation of Disaccharides Using Dibutylstannylene Acetals", *Tetrahedron Letters*, 35:35, 6563–6566 (1994).

Guilbert, B. et al., "Dibutylstannylene Acetals: Useful Intermediates for the Regioselective Sulfation of Glycosides", *Tetrahedron Asymmetry*, 5:11, 2163–2178 (1994).

Hara, A. et al., "Simple Procedures for the Rapid Cleavage of Ester Lipids and for the Large–Scale Isolation from Brain of Cerebroside Sulfate", *Analytical Biochemistry*, 100, 364–370 (1979).

Hemmerich, S. et al., "6'–Sulfated Sialyl Lewis x is a Major Capping Group of GlyCAM–1", *Biochemistry*, 33, 4830–4835 (1994).

Hudson, C.S. et al., "Relations Between Rotatory Power and Structure in the Sugar Group. X.$^2$ The Chloro–, Bromo–and Iodo–Acetyl Derivatives of Lactose", *U.S. Dept. of Commerce, Polarimetry Section, Bureau of Standards*, 47, 2052–2055 (1925).

Kartha, K.P.R. et al., "Synthetic Studies Toward Gangliosides and Their Analogs: Synthesis of Appropriately Protected Core Oligosaccharides as Construction Blocks", *J. Carbohydrate Chemistry*, 8:1, 145–158 (1989).

Kogelberg, H. et al., "Studies on the Three–Dimensional Behaviour of the Selectin Ligands Lewis and Sulphated Lewis Using NMR Spectroscopy and Molecular Dynamics Simulations", *Micobiology*, 4:1, 49–57 (1994).

Lander, A. D. et al., "Targeting the Glycosaminoglycan–Binding Sites on Proteins", *Chemistry & Biology*, 1:2, 73–78 (1994).

Langston, S. et al., "199. Temporary Protection and Activation in the Regioselective Synthesis of Saccharide Sulfates", *Helvetica Chimica ACTA*, 77, 2341–2553 (1994).

Leigh, D.A. et al., "Kinetically Controlled Regiospecific Silylation of Polyols via Dibutylstannanediyl Acetals", *J. Chem. Soc., Chem. Commun.*, 1373–1374 (1994).

(List continued on next page.)

Primary Examiner—Marian C. Knode
Assistant Examiner—Everett White
Attorney, Agent, or Firm—F. Brad Salcedo

[57] ABSTRACT

A direct method is disclosed for the regioselective sulfation of an organic molecule having optionally derivatized hydroxyl groups on at least two adjacent carbon atoms. The method comprises the treatment of a di-(optionally substituted alkyl and/or aryl) stannylene acetal derivative of the molecule with an electrophilic sulfating agent, preferably sulfur trioxide/trimethylamine. The disclosed method is useful for the selective sulfation of a variety of mono-, di- and oligosaccharides. Novel saccharides prepared according to this method are also disclosed.

4 Claims, No Drawings

OTHER PUBLICATIONS

Lubineau, A. et al., "Regioselective Sulfation of Galactose Derivatives Through the Stannylene Procedure. New Synthesis of the 3'–O–Sulfated Lewis$^a$ Trisaccharide.", *Tetrahedron Letters,* 35:47, 8795–8796 (1994).

Ludwig–Baxter, K.G. et al., "Regioselectivity in the Sulfation of Dermatan Sulfate and Methyl 4,6–O–Benzylidene–α–D–Idopyranoside", *Carbohydrate Research,* 214, 245–256 (1991).

Lubineau, A. et al., "First Synthesis of the 3'–Sulfated Lewis$^a$ Trisaccharides, Putative Ligand for the Leucocyte Homing Receptor", *J. Chem. Soc., Chem. Commun.,* 1419–1420 (1993).

Maccarana, M. et al., "Minimal Sequence in Heparin/Heparan Sulfate Required for Binding of Basic Fibroblast Growth Factor", *The J. of Biological Chem.,* 268:32, 23898–23905 (1993).

Munavu, R.M. et al., "Selective Formation of 2 Esters of Some Methyl–α–D–Hexopyranosides via Dibutylstannylene Derivatives", *J. Org. Chem.,* 41:10, 1832–1836 (1976).

Nashed, M.A. et al., "Orgaotin Derivatives and the Selective Acylation amd Alkylation of the Equatorial Hydroxy Group in a Vicinal, Equatorial–Axial Pair", *Tetrahedron Letters,* 39, 3503–3506 (1976).

Nicolaou, K.C. et al., Total Synthesis of Sulfated Le$^x$ and Le$^a$–Type Oligosaccharide Selectin Ligands, *J. Am. Chem. Soc.,* 115, 8843–8844 (1993).

Pankiewicz, K. W. et al., "(Triflouromethyl)sulfonyl (Triflyl) Migration. Synthesis of 6,3'–Anhydro–3–Benzyl–1–(5–chloro–5–deoxy–β–D–xylofuranosyl)barbituric Acid from the 2'–Triflouromethanesulfonate (Triflate) of 6,5'–Anhydro–3–Benzyl–1–β–D–Ribofuranosylbarbituric Acid", *J. Org. Chem.,* 51, 1525–1529 (1986).

Penney, C.L. et al., "A Method for the Sulfation of Sugars, Employing a Stable, Aryl Sulfate Intermediate", *Carbohydrate Research,* 93, 241–246 (1981).

Rashid, A. et al., "Novel Synthesis of Monosulphated Methyl α–D–Galactopyranosides", *Can. J. Chem.,* 68:7, 1122–1127 (1990).

Takano, R. et al., "Regioselectivity in Sulfation of Galactosides by Sulfuric Acid and Dicyclohexylcarbo–di–imide", *Bioscience, Biotechnology, and Biochemistry,* 56:9, 1413–1416 (1992).

Tsuda, Y. et al., "Regioselective Monotosylation of Non-protected and Partially Protected Glycosides by the Dibutyltin Oxide Method", *Chem. Pharm. Bull.,* 39:11, 2883–2887 (1991).

Tsuda, Y. et al., "Regioselective Monoacylation of Some Glycopyranosides via Cyclic Tin Intermediates", *Chem. Pharm. Bull.,* 31:5, 1612–1624 (1983).

Tsvetkov, Y.E. et al., "A Simple Preparation of Aromatic 1–Thioglycosides" *Carbohydrate Research,* 115, 254–258 (1983).

Unverzagt, C. et al., "High–Efficiency Synthesis of Sialyloligosaccharides and Sialoglycopeptides", *J. Am. Chem. Soc.,* 112, 9308–9309 (1990).

Wong, C. et al., "Probing the Acceptor Specificty of β–1, 4–Galactosyltransferase for the Development of Enzymatic Synthesis of Novel Oligosaccharides", *J. Am. Chem. Soc.,* 113, 8137–8145 (1991).

Yuen, C. et al., "Sulfated Blood Group Lewis", *J. of Biological Chemistry,* 269:3, 1595–1598 (1994).

Yuen, C. et al., "Novel Sulfated Ligands for the Cell Adhesion Molelcule E–Selectin Revealed by the Neoglycolipid Technology Among O–Linked Oligosaccharides on an Ovarian Cystadenoma Glycoprotein", *Biochemistry,* 31, 9126–9131 (1992).

Yasuri, M. et al., "Preparation of Acidic Glycolipids for Pharmaceutical Microparticle Carriers Such as Liposomes.", *Carbohydrates,* 120, 985 (1994).

Sedozai, K.K. et al., "Synthesis of Methyl 2–O–, 3–O–, 4–O–, 6–O–, 2,3–di–O–and 4,6–di–O–β–D–Galactopyranosyl–β–D–glocopyranoside. " *Carbohydrates,* 122, 1095 (1995).

Takiura, K. et al., "Arylsulfuryl Chloride Monosulfation"., *UDC,* 87, 1248–1255 (1967).

REGIOSELECTIVE SULFATION

This application is a 371 of PCT/EP95/03034 filed Jul. 27, 1995 published as WO96/03413 Feb. 8, 1996.

This invention relates to regioselective sulfation; more particularly, various sulfated organic molecules, some of which are novel, have been synthesised by a sulfation method via regioselective activation of the organic molecules to certain diorganostannylene acetals, followed by treatment with electrophilic sulfating agents.

Specifically, the present invention provides a direct method for the regioselective sulfation of an organic molecule having optionally derivatized hydroxyl groups at least on two adjacent carbon atoms characterised in that it comprises the treatment of a di -(optionally substituted alkyl and/or aryl) stannylene acetal derivative thereof with an electrophilic sulfating agent.

Conventional electrophilic sulfating agents may be used for the present purposes, for example sulfur trioxide/aminobase, such as pyridine or triethylamine, but sulfur trioxide/trimethylamine is preferred. The sulfation is conveniently effected at room temperature, e.g. 20°–25° C., in a suitable organic solvent, such as dioxane or THF. Of course, higher temperatures may be used if desired, depending upon the choice of solvent.

The present method involves the treatment of a stannylene acetal derivative of the starting material. Such derivatives are di- (optionally substituted alkyl and/or aryl substituted. In the case of an alkyl substituent, it is preferred that it contain up to six carbon atoms, while phenyl is an example of a suitable aryl substituent. Either may itself be substituted by one or more non-interfering substituents, e.g. alkoxyl. The substitution of the stannylene acetal derivatives may be dialkyl or diaryl or it may be alkyl - aryl. In a presently-preferred embodiment, a dibutylstannylene acetal derivative is used.

Generally, the present method may be carried out by conventional means, but an immobilised system may also be envisaged.

The starting material for the present method is an organic molecule having optionally derivatized hydroxyl groups at least on two adjacent carbon atoms. For example, ether-derivatization of one of the two hydroxyl groups may influence selectivity, more particularly in that the sulfate group would tend to be directed to the other position. More specifically, a 3'-sulfate would be expected to result from a galactoside or lactoside, while a 2'-sulfate may be obtained from a partially-protected maltoside.

In the absence of interfering substituents, the present methodology may be applied to a wide variety of such organic molecules. The presence of two hydroxyl groups in proximity, one of which is to be sulfated, is central to the present method. Saccharide chemistry is an instance where such selectivity may be important, particularly in view of the number of potentially-reactive hydroxyl groups. For example, the present method is well-suited to both poly- and oligo-saccharides, preferably containing no more than twenty, more preferably no more than six, repeating units. The advantages thereof are particularly apparent in relation to mono- and di- saccharides. The present method may be applied to glycoconjugates, such as glycolipids and glycopeptides, or to glycosaminoglycans. It should be noted that this methodology may also be used with analogues of the materials illustrated above, e.g. unnatural sugars, such as amino-sugars. As will be appreciated, there is no need to distinguish between natural and synthetic molecules or polymers.

In the exemplification of the present method, a number of novel compounds are identified below, specifically those numbered 14, 15, 16, 23, 25, 30, 32 and 34, and the present invention also relates thereto. As will be explained, compound 23 is of particular interest. Of course, such organic molecules may be conjugated to larger molecules and the present invention further relates thereto. This would also apply to other sulfate products of the present method.

One embodiment of the present invention concerns the regioselective sulfation of an oligosaccharide, preferably a mono- or di- saccharide, characterised in that it comprises the treatment of a dibutylstannylene acetal derivative thereof with sulfur trioxide/trimethylamine, a 3'-sulfate resulting from a galactoside or lactoside and a 2'-sulfate resulting from a partially-protected maltoside. Having discussed the present invention in general terms, it will now be further illustrated with particular reference to that exemplary embodiment.

In recent years, oligosaccharides and glycoconjugates containing sulfates and aminosulfonates have been isolated and characterised, and have been shown to play important roles in biological recognition processes. For example, 3'-O-sulfo-N-acetyllactosamide 1:

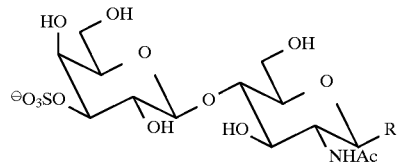

is a partial structure for the 3'-O-sulfo-Lewis$^x$ antigen which is recognised by E-selectins during the inflammatory response, (see, for example, Yuen, C. T., et al, Biochemistry, 31, 9126–9131, 1992; and Yuen C. T., et al, J. Biol. Chem., 269, 1595–1598; 1994). Compound 1 itself has been shown to be useful for detecting high levels of serum α-1,3-L-fucosyltransferase in ovarian cancer patients, since it is a selective substrate for this enzyme, (see, for example, Chadrasekaran, E. V., et al, J. Biol. Chem., 267, 23806–23814, 1992). Disaccharide 2:

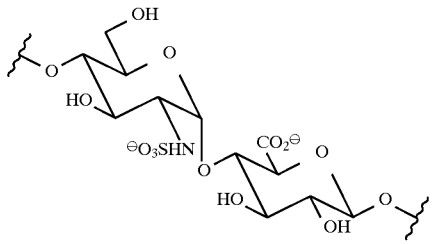

is a partial structure in heparan sulfate, which has recently been identified to be part of a specific basic fibroblast growth factor (bFGF) binding sequence, that participates in activation of bFGF and hence regulation of cell growth, (see, for example, Maccarana, M, et al, J. Biol. Chem., 268, 23898–23905, 1993). Galactosylceramide sulfatide 3:

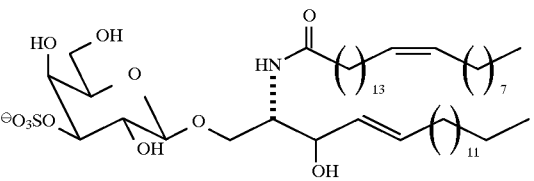

is a mammalian glycolipid, which has been isolated from spinal cord, (see, for example, Hara, A., and Radiu, N. S., Anal. Biochem., 100, 364–370, 1979).

The synthesis of natural sulfated oligosaccharides and of analogues containing various modifications is not trivial since it requires extensive protection and deprotection steps. For example, in the synthesis of structures related to 2, at least three orthogonal protection groups per monosaccharide unit have to be employed in synthesis: one for protecting the C-4 hydroxyl group, which needs to be selectively free for coupling; a second protecting group for those amino/hydroxyl groups which need to be sulfated during synthesis; and a third protecting group for those hydroxyl groups that remain free in the final product, (see, for example, Lubineau, A., et al, J. Chem. Soc. Chem. Commun., 1419–1420, 1993; and Nicolaou, K. C., et al, J. Am. Chem. Soc., 115, 8843–8844, 1993). There is a need to develop synthetic methods for complex carbohydrates which minimise the use of protecting groups by the use of highly regioselective reagents and this has led to the development of regioselective sulfation using the well known dibutylstannylene acetals of glycosides as activated intermediates, (see, for example, Guilbert, B., et al, Tet. Lett., 35, 6563–6566, 1994).

Dibutyltin oxide is known to form five-, sometimes six- or seven-, membered cyclic dibutylstannylene acetals with saccharides, preferably with cis diol configurations, (see, for example, Tsuda, Y., et al, Chem. Pharm. Bull., 39, 2883–2887, 1991; and David, S and Hanessian, S., Tetrahedron, 41, 643–663, 1985). In such complexes, the nucleophilicity of one hydroxyl group is often enhanced, (see, for example, Nashed, M. A., and Anderson, L., Tet. Lett., 39, 3503–3506, 1976), towards acylation, alkylation, tosylation or silylation, (see, for example, David, S., and Hanessian, S., loc cit; Glen, A., et al, Carbohydr. Res., 248, 365–369, 1993; and Leigh D. A., et al, J. Chem. Soc. Chem. Commun., 1373–1374, 1994). For example, the unprotected β-lactoside 4 was converted exclusively to the 3'-O-derivative 5 via the reaction of its 3',4'-dibutylstannylene acetal with allyl or benzyl bromide, (see, for example, Alais, J., et al, Tet. Lett., 24, 2383–2386, 1983; and Kartha, K. P. R., et al, J. Carbohydr. Chem., 8, 145–158, 1989):

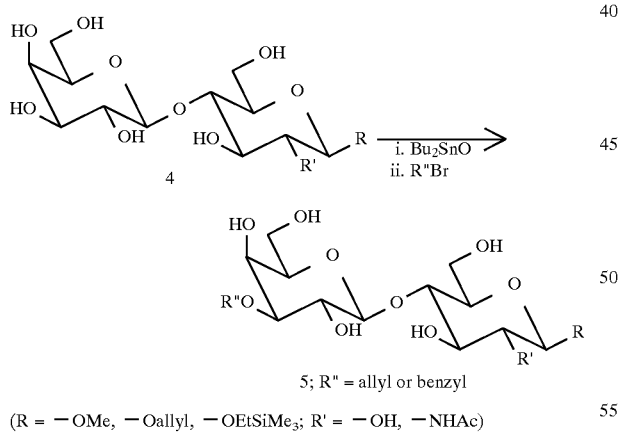

(R = —OMe, —Oallyl, —OEtSiMe₃; R' = —OH, —NHAc)

In the case of silylation, the reversible migration of the stannylene acetal from the 3',4' positions to either the 4',6' or ring oxygen, 6' positions lead to the 6'-O-derivative, (see, for example, Glen, A., et al, loc cit; and Leigh, D. A., et al, loc cit). When using α-glycosides containing no cis diols, or when the cis diols are protected, the dibutylstannylene acetal may complex the 2 position and the anomeric oxygen to give the 2-O-derivative by reaction with an electrophile, (see, for example, Munavu, R. M., and Szmant, H. H., J. Org. Chem., 41, 1832–1836, 1976; and Tsuda, Y., et al, Chem. Pharm. Bull., 31, 1612–1624, 1983).

The regioselective sulfation of phenyl thio-β-lactoside 8 was initially studied, as it is easily obtained from bromolactose heptaacetate and thiophenol, (see, for example, Hudson, C. S., and Kunz, A., J. Am. Chem. Soc., 47, 2052–2055, 1925; and Tsvetkov, Y. E., et al, Carbohydr. Res., 115, 254–258, 1983), following by conventional deacetylation:

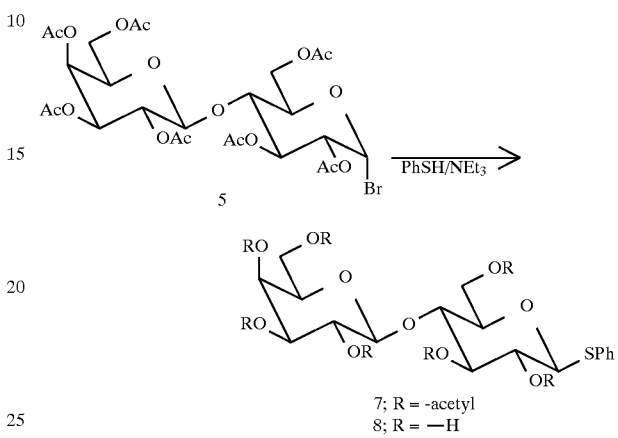

The stannylene acetal complex was prepared by stirring 8 with dibutyltin oxide in refluxing methanol and removing the solvent in vacuo. The initial aim was to introduce the sulfate in a protected form, such as the phenylsulfate group, which had already been used with saccharides, (see, for example, Takiura, K., and Honda, S., Yakugaku Sasshi, 87, 1248–1255, 1967; and Penney, C. L., and Perlin, A. S., Carbohydr. Res., 93, 241–246, 1981). Because of its structural similarity to phenylchlorosulfate, reactions with tosylchloride were first investigated, in order to establish that tosylation follows the same regioselectivity as acylation. Thus, the dry dibutylstannylene acetal prepared from 8 was treated with 15 equivalents of tosyl chloride and 0.5 equivalent of tetrabutyl ammonium bromide in refluxing THF. Bromide anions are known to activate the reaction by nucleophilic substitution on the tin complex, (see, for example, Alais, J., and Veyrieres, A., J. Chem. Soc., Perkin Trans. I, 377–381, 1981). The reaction occurred readily giving the 3'-O-tosyl derivative 9 as the major isolated product (~75%) and the 3',6'-di-O-tosyl lactoside 11 as the minor product (~15% yield):

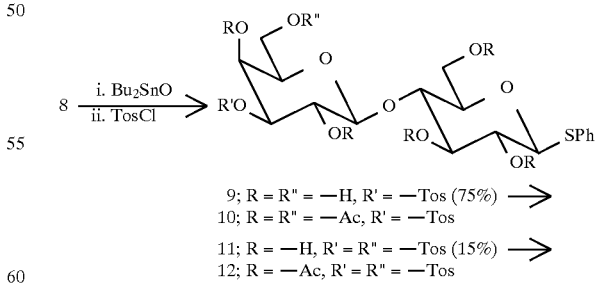

The formation of 11 could be due to initial tosylation at the 3' position with migration of the stannylene acetal to activate the 6' position towards a second tosylation. The $^1$H NMR spectrum of 9 and 11 confirmed the presence of one and two tosyl groups, respectively, and the regioselectivity of tosylation was confirmed by the downfield shift of the 3'-H in 9 and of 3'-H and 6'-H in 11. Unambiguous characterisation of 9 and 11 was possible after peracetylation to 10 and 12, respectively. Thus, tosylation seemed to have occurred with similar regioselectivity as reported for benzylation and allylation (see, for example, Alais, J., et al, loc cit; and Kartha, K. P. R., et al, loc cit).

The next step was to look at the reaction of phenylchlorosulfate 13, (see, for example, Penney, C. L., and Perlin, A. S., loc cit), with the stannylene acetal of 8. However, analysis of the reaction mixture by thin layer chromatography revealed that the reaction had not gone to completion and that a mixture of products had been formed. Only compound 14 containing a 6'-O-sulfate group could be isolated from this mixture in ~11% yield:

Scheme 4

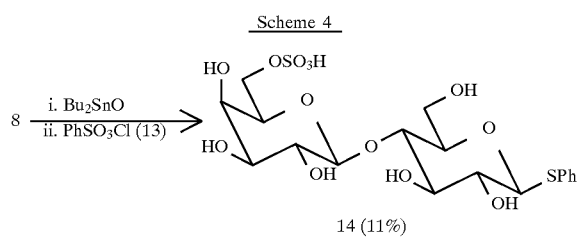

14 (11%)

14 had presumably been formed by decomposition of the corresponding 6'-O-phenylsulfate. Thus, reaction of the stannylene acetal of 8 with phenyl chlorosulfate had shown less selectivity than the corresponding tosylation and had given as a main product the 6' isomer instead of the 3' sulfate. Since this might be explained by the lower reactivity of the phenylchlorosulfate, the reaction was repeated with the more reactive p-nitrophenylchlorosulfate, again with little success.

As a more reactive sulfation reagent, and one which should yield stable products, $Me_3N.SO_3$ was chosen to react with the dibutylstannylene acetal of 8. This reaction proved to be unexpectedly successful. Thus, treatment with two equivalents of $Me_3N.SO_3$ in dioxane at room temperature for 30 hours resulted in the conversion of the dibutylstannylene acetal of 8 to the 3'-O-sulfo-lactoside 15 (~76%) and the 3',6'-di-O-sulfo-lactoside 16 (~10%), both isolated as the sodium salts thereof:

Scheme 5

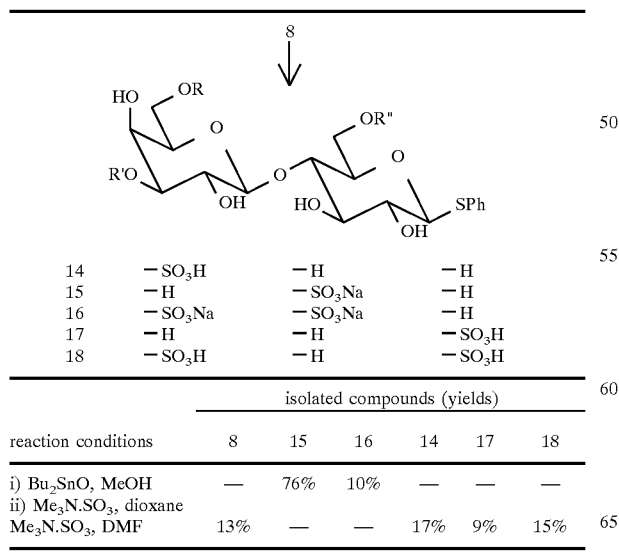

| | | | |
|---|---|---|---|
| 14 | —SO₃H | —H | —H |
| 15 | —H | —SO₃Na | —H |
| 16 | —SO₃Na | —SO₃Na | —H |
| 17 | —H | —H | —SO₃H |
| 18 | —SO₃H | —H | —SO₃H |

| | isolated compounds (yields) | | | | | |
|---|---|---|---|---|---|---|
| reaction conditions | 8 | 15 | 16 | 14 | 17 | 18 |
| i) Bu₂SnO, MeOH ii) Me₃N.SO₃, dioxane | — | 76% | 10% | — | — | — |
| Me₃N.SO₃, DMF | 13% | — | — | 17% | 9% | 15% |

In this reaction addition of bromide anions was unnecessary as the trimethylamine presumably took the role of activating the tin complex towards electrophilic attack. The selectivity is the same as that observed with allyl, benzyl or tosyl halides and would be expected to proceed via the same 3',4' stannylene acetal intermediate. The presence of a sulfate group may be observed by NMR spectroscopy in that it causes a downfield shift of 3'-H and 4'-H to 4.01 and 3.87–3.89 ppm, respectively, (see, for example, Kogelberg, H., and Rutherford, T., Glycobiology, 4, 49–57, 1994), in 15 compared to 8, and also of 6'-H in 16. The structure of 15 was also confirmed by independent synthesis via an alternative conventional five step route from 8, which lead to a product having identical spectroscopic data.

Since $Me_3N.SO_3$ may react with hydroxyl groups without the need for an added base, the reaction of 8 therewith was investigated to establish that the observed selectivity was indeed due to activation by the tin complex. Firstly, no reaction was observed with the lactoside 8 was merely stirred under similar conditions (in dioxane) with $Me_3N.SO_3$, possibly due to the poor solubility of 8 in this solvent. However, sulfation proceeded when a solution of 8 in DMF was treated with two equivalents of $Me_3N.SO_3$. Contrary to the previous reaction, a mixture of at least three products, 14, 17 and 18, in addition to starting material was formed, notably none of them containing a sulfate at the 3' position. This confirmed that activation by dibutyltin oxide was necessary for the observed regioselectivity of sulfation.

This methodology of selected sulfation was applied to the synthesis of sulfated N-acetyl lactosaminide 23, the thiophenyl glycoside of 1. Thiophenyl N-acetyllactosaminide 21 is not commercially available and was prepared by enzymatic galactosylation of 20 using β-1,4-galactosyltransferase from bovine milk. As an aside, it is interesting to note that it has previously been reported that 20 is not a substrate for this enzyme, (see, for example, Wong, C. H., et al, J. Am. Chem. Soc. 113, 8137–8145, 1991), but gave 21 in good isolated yield (~60%) using previously described procedures, (see, for example, Guilbert, B., and Flitsch, S. L., J. Chem. Soc., Perkin Trans. I, 1181–1186, 1994; Wong, C. H., et al, J. Org. Chem., 47, 5416–5418, 1982; and Unverzagt, C., et al, J. Am. Chem. Soc., 112, 9308–9309, 1990):

Scheme 6

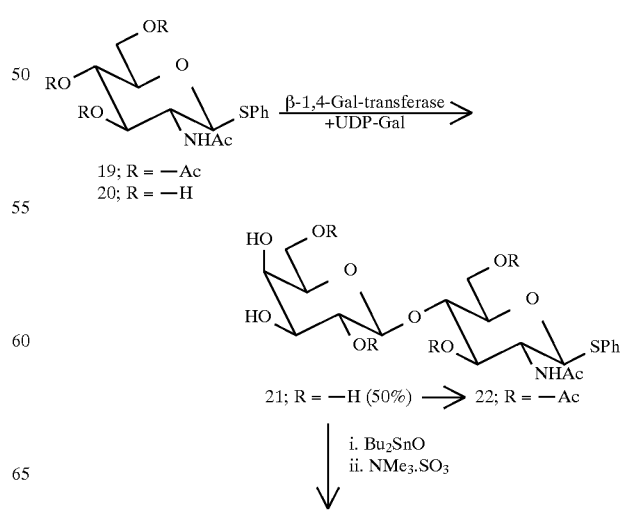

-continued
Scheme 6

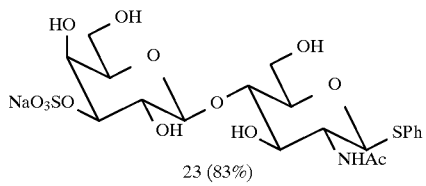

23 (83%)

These results might be due to the higher concentration of enzyme and acceptor (1 U/ml; 40 mM) as compared to the previous study (40 mU/ml; 25 mM). The 1,4 linkage in 21 was confirmed by NMR studies after acetylation. Treatment of 21 with acetic anhydride/pyridine at room temperature gave, after 45 hours, 22 which surprisingly contained free 3' and 4' hydroxyl groups. Nevertheless, the relevant ring protons in 22 showed a suitable spread of NMR signals to make NOE experiments possible. Upon acetylation of 21 to 22, the 4-H signal was not shifted downfield and irradiation of 1'-H and 6'-Hb at 4.38 ppm caused 4.7% enhancement of the 4-H signal and as expected of 5'-H, 3'-H (7%) and 6'-Ha (8%) confirming the existence of a 1,4-linkage in 22.

Sulfation of the dibutylstannylene acetal of 21 in THF with $Me_3N.SO_3$ gave exclusively the 3'-O-sulfated compound 23 in 83% isolated yield. Interestingly, no formation of other side-products, as found for the sulfation of the corresponding lactoside 8, was observed. NMR and high resolution mass spectrometry data were in agreement with the 3' sulfated compound 23. The synthesis of 23 illustrates a particularly useful feature of the present sulfation method in that it may easily be combined with enzymatic methodologies.

The present sulfation method was further applied to the synthesis of various mono- and di-saccharides as exemplified in Table 1 below. Sulfation of the methyl β-galactoside 24 was very selective giving 25 in 93% isolated yield. The structure was confirmed by NMR spectroscopy (COSY) in the peracetylated derivitve 26. The method is also applicable to the synthesis of glycolipids, such as the sodium salt of 3. Thus, galactosylceramide 27 was selectivity sulfated in 97% isolated yield with a trace of the 3',6'-disulfated side-product 28 being formed. It is interesting to note that the allylic hydroxyl group on the ceramide did not react. The synthesis of glycolipids using glycosyltransferase enzymes has been described in WO 93/20226. The present method relates to the elaboration of such glycolipid structures where the sialic acid moiety may potentially be substituted by a sulfate. Such sulfated molecules may exhibit similar biological properties with the advantage of simple, less costly synthesis.

Also, the selective sulfation of maltosides, such as 29, 31 and 33, (see, for example, Davies, N. J., DPhil thesis, Oxford, 1994), were investigated in connection with the synthesis of heparan sulfate fragments, such as 2, (see, for example, Davies, N. J., and Flitsch, S. L., J. Chem. Soc., Perkins Trans I, 359–368, 1994). Selective sulfation at the desired 2' position of these maltosides to 30, 32 and 34, respectively, was indeed achieved in medium to good yields.

TABLE 1

Regioselective Sulfation of Various Saccharides Using the Present Methodology

| STARTING MATERIAL | PRODUCT (YIELD) |
|---|---|
| 24 | 25 (93%) |
| 27 | 3: R = —H (97%)<br>28: R = —SO₃Na (trace) |
| 29; R = —Bn, R' = —CH₂OH<br>31; R = -allyl, R' = —CO₂tert-Bu<br>33; R = -allyl, R' = —CH₂OSitert-BuMe₂ | 30; R = —Bn, R' = —CH₂OH (87%)<br>32; R = -allyl, R' = —CO₂tert-Bu (54%)<br>34; R = -allyl, R' = —CH₂OSitert-BuMe₂ (56%) |

In summary, it has been shown that the activation of selected hydroxyl groups in unprotected or partially protected saccharides by dibutyltin oxide may lead to selectively sulfated saccharides in good to excellent yields. The present methodology may be applied in the synthesis of a variety of natural products. It may be applicable to the sulfation of other hydroxyl groups, in particular for the synthesis of 6-sulfated saccharides, (see, for example, Hemmerich, S., and Rosen, S. D., Biochemistry, 33, 4830–4835, 1994) and to the sulfation of higher saccharides.

6-O-sulfation may be achieved by either varying the ligands on the tin, e.g. by using $(Bu_3Sn)_2O$ as the activating reagent inwstead of $Bu_2SnO$, or by varying the sulfation reagent $Me_3N.SO_3$, as had already been shown when 13 was used as the sulfation reagent and 6-O-sulfation was achieved (see Scheme 4 above).

The present invention is further illustrated by the following.

EXPERIMENTAL

General—Reactions were carried out in solvents distilled from standard drying agents; thin layer chromatography was performed on aluminium sheets silica gel $60F_{254}$ (Merck, layer thickness 0.2 mm); the components were detected by heating the TLC after spraying with a solution of 5% sulfuric acid-5% anisaldehyde in ethanol; silica gel C60 (Merck, 40–60 μm) was used for flash chromatography; NMR spectra were recorded on Bruker AM-500 MHz, Varian Gemini 200 MHz or Bruker AM 200 MHz spectrometers using solvents as stated; Coupling constants J are in Herz: IR spectra were recorded on a Perkin-Elmer 1750 spectrometer and optical rotations on a Perkin-Elmer 241 polarimeter; mass spectrometry was carried out on VG Analytical Ltd, ZABIF or BIO-Q mass spectrometers using chemical impact ($CI/NH_3$), ammonia desorption chemical ionisation ($DCI/NH_3$), positive argon fast atom bombardment (FAB) and negative electrospray ($ES^-$) as indicated; high resolution mass spectra were recorded on a VG AutospecEQ spectrometer ($FAB^-$), Brucker FTICR using matrix assisted laser desorption ionisation (MALDI) or liquid secondary ionisation mass spectrometry (LSIMS) or by the EPSRC mass spectrometry service centre at Swansea; uridine 5'-diphospholgucose (UDP-glucose), uridine 5'-diphospho-glucose 4-epimerase (EC 5.1.3.2), β-1,4-galactosyltransferase from bovine milk (EC 2.4.1.22) and galactocerebroside (Type II, contains primarily nervonic acid) were purchased from Sigma; calf intestinal alkaline phosphatase (CIAP) (EC 3.1.3.1) and bovine serum albumin (BSA) were obtained from Boehringer Mannheim.

Phenyl 2,3,6-tri-O-acetyl-4-O-(2',3',4',6'-tetra-O-acetyl-β-D-galactopyranosyl)-1-deoxy-1-thio-β-D-glucopyranoside 7:

A solution of heptaacetobromo-α-D-lactose (3.70 g, 5.29 mmol) in $CH_3CN$ (20 ml) was stirred with thiophenol (0.652 ml, 6.35 mmol) and thiethylamine (1.5 ml, 10.59 mmol) at room temperature for 18 hours. The reaction mixture was filtered, reduced in vacuo and purified by chromatography ($CH_2Cl_2/Et_2O$ 9:1) to give 7 as a white solid (3.24 g, 84%): $[α]^{24}_D$+5 (c 20 in $CHCl_3$); m.p. 161° C.: Rf 0.07 ($CH_2Cl_2/Et_2O$ 9:1); $v_{max}$ ($CHCl_3$)/cm$^{-1}$ 2902–2985 (CH), 1753 (CO); $δ_H$(500 MHz; $CDCl_3$) 1.96 and 2.03 (6H, 2×s, 2×Ac), 2.04 (6H, 2×s, 2×Ac), 2.09, 2.11, 2.15 (9H, 3×s, 3×Ac), 3.64 (1H, ddd, J 2.0, 5.6, 9.9, 5-H), 3.75 (1H, dd, J 9.5, 9.5, 4-H), 3.86 (1H, ddd, J, 1.0, 7.3, 7.3, 5'-H), 4.05–4.14 (3H, m, 6-Ha, 6'-Ha, 6'-Hb), 4.48 (1H, d, J 7.9, 1'-H), 4.53 (1H, dd, J 2.0, 11.9, 6-Hb), 4.68 (1H, d, J 10.1, 1-H), 4.90 (1H, dd, J 9.6, 9.6, 2-H), 4.95 (1H, dd, J 3.4, 10.4, 3'-H), 5.10 (1H, dd, J 7.9, 10.4, 2'-H), 5.22 (1H, dd, J 9.1, 9.1, 3-H), 5.34 (1H, dd, J 0.9, 3.4, 4'-H), 7.28–7.33 (3H, m, Ph), 7.43–7.50 (2H, m, Ph); $δ_C$(50 MHz, $CDCl_3$) 20.35, 20.47, 20.62 (7 $CH_3$), 60.79, and 62.10 (2 $CH_2$), 66.59, 69.04, 69.93, 70.21, 70.74, 73.82, 76.13, and 76.55 (8 CH), 85.45 (1-C), 101.08 (1'-C), 128.45 (CH, Ph), 129.06 (2 CH, Ph), 131.93 (C), 133.05 and 133.17 (2 CH, Ph), 169.31, 169.83, 169.98, 170.32 and 170.42 (5 CO), 170.60 (CO); m/z(DCI) 746 ($MNH_4^+$, 7%), 331 [(M-397)$^+$, 100].

Phenyl 1-deoxy-4-O-(β-D-galactopyranosyl)-1-thio-β-D-glucopyranoside 8:

To a solution of 7 (3.23 g, 4.43 mmol) in $CH_2Cl_2$/MeOH (1:1.4, 24 ml) was added a 0.2M sodium methoxide solution (8.85 ml, 1.77 mmol). The reaction mixture was stirred at room temperature for 1.7 h, neutralized with amberlite IR-120 (H) resin, filtered and concentrated in vacuo to 5 ml leading to the precipitation of 8 as a white solid which was collected by filtration (1.58 g, 82%). The filtrate was reduced in vacuo and chromatographed (MeOH/$CHCl_3/H_2O$ 4:5:1) to give compound 8 (222 mg, 12%): $[α]^{24}_D$−44.3 (c 1.5 in MeOH); m.p. 126° C.; Rf 0.33 (MeOH/$CHCl_3/H_2O$ 4:5:1); $v_{max}$ (KBr)/cm$^{-1}$ 3402 (OH), 2940–2880 (CH); $δ_H$(500 MHz; $CD_3OD$) 3.28 (1H, dd, J 8.6, 9.6, 2-H), 3.43–3.46 (1H, m, 5-H), 3.48 (1H, dd, J 3.3, 9.7, 3'-H), 3.52–3.59 (4H, m, 3-H, 4-H, 2'-H, 5'-H), 3.69 (1H, dd, J 4.6, 11.5, 6'-Ha), 3.77 (1H, dd, J 7.5, 11.5, 6'-Hb), 3.81 (1H, d, J 3.2, 4'-H), 3.83 (1H, dd, J 4.3, 12.3, 6-Ha), 3.90 (1H, dd, J 2.5, 12.3, 6-Hb), 4.36 (1H, d, J 7.6, 1'-H), 4.61 (1H, d, J 9.8, 1-H), 7.24–7.32 (3H, m, Ph), 7.54–7.57 (2H, m, Ph); $δ_C$(50 MHz, $CD_3OD$) 61.39 and 61.92 (2 $CH_2$), 69.78, 72.02, 72.90, 74.24, 76.58, 77.45, 79.63, 80.01 (8 CH), 88.66 (1-C), 104.39 (1'-C), 128.10 (CH, Ph), 129.55 (2 CH, Ph), 132.63 (2 CH, Ph), 134.28 (C, Ph); m/z ($FAB^+$) Found: 457.1145 ($MNa^+$), $C_{18}H_{26}O_{10}SNa^+$ requires 457.1144.

Phenyl 1-deoxy-1-thio-4-O-(3'-O-p-toluenesulfonyl-β-D-galactopyranosyl)-β-D-glucopyranoside 9 and Phenyl 1-deoxy-1-thio-4-O-(3'-6'-di-O-p-toluenesulfonyl-β-D-galactopyranosyl)-β-D-glucopyranoside 11:

Compound 8 (50 mg, 115 μmol) and $Bu_2SnO$ (43 mg, 169 μmol) were stirred in refluxing MeOH (1 ml), under nitrogen for 1 hours. The solvent was removed in vacuo and the dry dibutylstannylene complex was dissolved in THF (1 ml), $Bu_4NBr$ (18.5 mg, 58 μmol) and p-toluenesulfonyl chloride (329 mg, 1.72 mmol) were added and the mixture heated under reflux for 1 hours. The solvent was removed in vacuo and the residue chromatographed ($CH_2Cl_2$/MeOH 10:1) to give some starting material (4.7 mg, 9%), 9 as a colorless oil containing some butylstannyl derivatives (54.5 mg, ~75%) and 11 which was chromatographed again twice ($CH_2Cl_2/Et_2O$ 10:1, then $CH_2Cl_2/Et_2O$ 17:1) leading to a colourless gum (12.8 mg, 15%): 9: Rf 0.09 (MeOH/$CH_2Cl_2$ 1:10); $v_{max}$ ($CDCl_3$)/cm$^{-1}$ 3369 (OH), 2966, 2878 (CH), 1599 (C=C), 1354, 1177 ($SO_2$): $δ_H$(500 MHz; $CDCl_3$) 2.38 (3H, s, Me), 3.27 (1H, m, OH), 3.43–3.45 (2H, m, 2-H, 5-H), 3.58–3.59 (1H, m, 5'-H), 3.67–3.72 (2H, m, 3-H, 4-H), 3.80–3.88 (4H, m, 6-Ha, 6-Hb, 6'-Ha, 6'-Hb), 3.97 (1H, dd, J 9.1, 13.2, 2'-H), 4.09 (1H, s, 4'-OH), 4.18 (1H, s, OH), 4.29 (1H, s, 2'-OH), 4,43–4.50 (3H, m, 3'-H, 2×OH), 4.51 (1H, d, J 7.8, 1'-H), 4.67 (1H, d, J 9.7, 1-H), 5.10 (1H, s, OH), 7.22–7.29 (5H, m, Ar), 7.50 (2H, d, J 6.9, Ar), 7.82 (2H, d, J 8.2. Ar); $δ_C$125.78 MHz, $CDCl_3$) 21.64 ($CH_3$), 61.29 and 61.55 (2 $CH_2$), 68.03, 68.27, 72.13, 74.24, 76.34, 78.46 and 82.85

(7 CH), 87.41 (1-C), 103.13 (1'-C), 128.00 (2 CH), 128.89 (3 CH), 129.90 (2 CH), 131.96 (2 CH), 132.94 (C, Ts), 133.22 (C, Ph), 144.94 (C, Ts); m/z (FAB$^+$) 573 [(M-CH$_3$)$^+$, 1%], 471 [(M-117)$^+$, 18], 242[(M-346)$^+$, 53], 155 [(M-433)$^+$, 87], 91 (CH$_3$Ph$^+$, 100); 11: [a]$^{25}_D$–14.9 (c 2.3 in MeOH); Rf 0.40 (MeOH/CH$_2$Cl$_2$ 1:1); $v_{max}$ (CDCl$_3$)/cm$^{-1}$ 3500 (OH), 2960, 2880 (CH), 1599 (C=C), 1366, 1178 (SO$_2$); $\delta_H$(500 MHz; CDCl$_3$) 2.43 (6H, s, 2×Me), 2.80 (1H, t, J 6.0, 6-OH), 3.19 (1H, d, J 2.2, 2-OH), 3.23 (1H, d J 4.6, 4'-OH), 3.38–3.44 (2H, m, 2-H, 5-H), 3.57–3.65 (2H, m, 3-H, 4-H), 3.83–3.90 (5H, m, 2'-H, 2'-OH, 5'-H, 6-Ha, 6-Hb), 4.04 (1H, dd, J 3.7, 3.9, 4'-H), 4.09 (1H, d, J 1.3, 3-OH), 4.17 (1H, dd, J 7.1, 10.6, 6'-Ha), 4.21 (1H, dd, J 5.3, 10.7, 6'-Hb), 4.43–4.47 (2H, m, 1'-H, 3'-H), 4.59 (1H, d, J 9.8, 1-H), 7.28–7.51 (7H, m, Ar), 7.51 (1H, d, J 1.7, Ar), 7.52 (1H, d, J 2.2, Ar), 7.78 (2H, d, J 8.3, Ar), 7.83 (2H, d, J 8.3, Ar); $\delta_C$(125.78 MHz, CDCl$_3$) 21.64 (2 CH$_3$), 61.91 (CH$_2$), 67.11 (CH), 67.69 (CH$_2$), 68.29 (CH), 71.84 (CH), 71.91 (CH), 76.18 (CH), 78.16 (CH), 79.95 (CH), 82.08 (CH), 87.42 (1-C), 103... (1'-C), 128.03 (4 CH), 128.98 (2 CH), 130.02 (5 CH), 132.02 (C, Ts), 132.16 (C, Ts), 132.48 (2 CH), 132.72 (C, Ph), 145.39 (C, Ts), 145.53 (C, Ts); m/z (MALDI) Found: 765.1309 (MNA$^+$), C$_{32}$H$_{38}$S$_3$O$_{14}$Na$^+$ requires 765.1321.

Phenyl 2,3,6-tri-O-acetyl-4-O-(2',4',6'-tri-O-acetyl-3'-p-toluenesulfonyl-β-D-galactopyranosyl)-1-deoxy-1-thio-β-D-glucopyranoside 10:

Crude compound 9 (15.3 mg, <26 μmol) was stirred in pyridine/Ac$_2$O 2:1 (300 μl), at room temperature for 20 hours. The reaction mixture was reduced in vacuo and chromatographed [petroleum ether (b.p. 40°–60° C.)/ethyl acetate 1:1] leading to 10 as a colourless foam (14.2 mg, 65%): [α]$^{25}_D$–3.0 (c 0.9 in CHCl$_3$); Rf 0.26 [petroleum ether (b.p. 40°–60° C.)/ethyl acetate 1:1]; $v_{max}$ (CHCl$_3$)/cm$^{-1}$ 2960, 2860 (CH), 1753 (C=O), 1599 (C=C), 1373, 1179 (SO$_2$), 1225 (C-O); $\delta_H$(500 MHz, CDCl$_3$) 1.93, 2.01, 2.04, 2.05, 2.08, 2.11 (18H, 6×s, 6×Ac), 2.44 (3H, s, Me), 3.63 (1H, ddd, J 2.0, 5.7, 9.9, 5-H), 3.73 (1H, dd, J 9.6, 9.6, 4-H), 3.83 (1H, t, J 6.6, 5'-H), 4.05 (2H, d, J 6.7, 6'-Ha, 6'-Hb), 4.09 (1H, dd, J 5.8, 11.9, 6-Ha), 4.48 (1H, d, J 7.9, 1'-H), 4.51 (1H, dd, J 2.0, 11.9, 6-Hb), 4.67 (1H, d, J 10.1, 1-H), 4.72 (1H, dd, J 3.6, 10.1, 3'-H), 4.89 (1H, dd, J 9.7, 9.7, 2-H), 5.06 (1H, dd, J 7.9, 10.1, 2'-H), 5.20 (1H, dd, J 9.1, 9.1, 3-H), 5.45 (1H, d, J 3.5, 4'-H), 7.29–7.34 (5H, m, Ar), 7.46–7.48 (2H, m, Ar), 7.73 (2H, d, J 8.3, Ar); $\delta_C$(125.78 MHz, CDCl$_3$) 20.50 (2 CH$_3$), 20.63 (CH$_3$), 20.76 (2 CH$_3$), 20.84 (CH$_3$), 21.68 (CH$_3$), 60.84 and 62.08 (2 CH$_2$), 67.24, 68.99, 70.24, 70.71, 73.79, 76.17, 76.32 and 76.61 (8 CH), 85.46 (1-C), 100.74 (1'-C), 127.98 (2 CH), 128.31 (CH), 128.88 (2 CH), 129.80 (2 CH), 131.74 (C, Ts), 132.90 (C, Ph), 133.03 (2 CH), 145.34 (C, Ts), 169.00, 169.39, 169.55, 169.63, 170.24 and 170.33 (6 CO); m/z (FAB$^+$) 863 (MNa$^+$, 6%), 841 (MH$^+$, 3), 731 [(M-SPh)$^+$, 17], 443 [(M-397)$^+$, 18], 169 [(M-671)$^+$, 33], 109 (PhS$^+$, 34), 43 (CH$_3$CO$^+$, 100).

Phenyl 2,3,6-tri-O-acetyl-4-O-(2',4'-di-O-acetyl-3',6'-di-O-p-toluenesulfonyl-β-D-galacto-pyranosyl)-1-deoxy-1-thio-β-D-glucopyranoside 12:

11 (11.3 mg, 15 μmol) was treated as described for the synthesis of 10 to give 12 as a gum (14 mg, 97%): [α]$_D^{25}$+1.8 (c 0.9 in CHCl$_3$); Rf 0.35 [petroleum ether (b.p. 40°–60° C.)/ethyl acetate 1:1]; $v_{max}$ (CHCl$_3$)/cm$^{-1}$ 2950, 2880 (CH), 1756 (C=O). 1599 (C=C), 1373, 1179 (SO$_2$), 1225 (C-O); $\delta_H$(500 MHz; CDCl$_3$) 1.91, 1.94, 1.98, 2.09, 2.10 (15H, 5×s, 5×Ac), 2.48 (6H, 2×s, 2×Me), 3.63 (1H, ddd, J 1.8, 5.5, 9.8, 5-H), 3.72 (1H, dd, J 9.7, 9.7, 4-H), 3.87 (1H, t, J 6.3, 5'-H), 3.98 (2H, d, J 6.3, 6'-Ha, 6'-Hb), 4.06 (1H, dd, J 5.6, 11.9, 6-Ha), 4.46 (1H, d, J 7.9, 1'-H), 4.50 (1H, dd, J 1.9, 12.0, 6-Hb), 4.67 (2H, d, J 10.1, 1-H and dd, J 2.1, 10.1, 3'-H), 4.88 (1H, dd, J 9.7, 9.7, 2-H), 5.03 (1H, dd, J 7.9, 10.2, 2'-H), 5.19 (1H, dd, J 9.1, 9.1, 3-H), 5.40 (1H, d, J 3.5, 4'-H), 7.29–7.32 (3H, m, Ar), 7.34 (2H, d, J 8.2, Ar), 7.38 (2H, d, J 8.2, Ar), 7.48 (2H, dd, J 2.5, 6.1, Ar), 7.72 (2H, d, J 8.3, Ar), 7.77 (2H, d, J 8.3, Ar); $\delta_C$(125.78 MHz, CDCl$_3$) 20.34, 20.47, 20.68, 20.78 and 20.84 (5 CH$_3$), 21.70 (2 CH$_3$), 62.01 and 65.82 (2 CH$_2$), 67.26, 68.86, 70.30, 70.97, 73.63, 75.96, 76.18 and 76.54 (8 CH), 85.36 (1-C), 100.39 (1'-C), 127.98 (2 CH), 128.00 (2 CH) 128.26 (CH), 128.89 (2 CH), 129.85 (2 CH), 130.09 (2 CH), 131.77 and 132.15 (2 C, Ts), 132.88 (2 CH, 1C), 145.42 and 145.52 (2C, Ts), 168.95, 169.19, 169.50, 169.65 and 170.32 (5 CO); m/z (LSIMS) 843[(M-SPh)$^+$, 5%], 55[(M-397)$^+$, 42], 281[(M-671)$^+$, 100].

Phenylchlorosulfate 13:

A solution of phenol (17 g, 181 mmol) in dry toluene (380 ml) was stirred with sodium pieces (4.15 g, 180 mmol) in a 100° C. oil bath for 2 hours. When hydrogen formation had finished, the oil bath temperature was increased to 130° C. for two more hours. The reaction mixture was cooled to 0° C. transferred to a pressure equalising funnel and added slowly (1 h) to a cold (0° C.) solution of sulfuryl chloride (15 ml, 181 mmol) in toluene (50 ml). The reaction mixture was stirred at room temperature for 16 h, washed with H$_2$O (3×100 ml), dried over Na$_2$SO$_4$ and concentrated in vacuo leading to a brown oil which was distilled under reduced pressure through a Vigreux column (70°–72° C./100 μm Hg, lit[13a]; 61°–65° C./50 μm Hg) to give a fraction of colourless oil containing 13 and ~10% penol (23.3 g, 67%), and a small fraction of pure I3 (1.17 g, 3%): $v_{max}$ (CDCl$_3$) 1587 (C=C). 1201 (SO$_3$); $\delta_H$(200 MHz; CDCl$_3$) 7.34–7.57 (m, Ph); $\delta_C$(50 MHz, CDCl$_3$) 121.69 (2 CH), 123.15 (C), 128.84 (CH), 130.28 and 130.42 (2 CH); m/z (EI) 194 (M$^+$, 14%). 192 (M$^+$, 38), 93[(M-SO$_2$Cl)$^+$, 33], 65 [(M-127)$^+$, 100].

Phenyl 1-deoxy-4-O-(6'-O-sulfo-β-D-galactopyranosyl)-1-thio-β-D-glucopyranoside 14:

8 (50 mg, 115 μmol) was treated as described for the synthesis of 9 and 11, but using PhSO$_3$Cl (239 μl, 1.7 mmol) instead of p-toluenesulfonyl chloride. Chromatography (MeOH/CHCl$_3$/H$_2$O 4:5:1) gave the unreacted starting material and 14 (6.5 mg, 11%) as a white solid: m.p. 176° C. (dec.); Rf 0.27 (MeOH/CHCl$_3$/H$_2$O 4:5:1); $v_{max}$ (KBr)/cm$^{-1}$ 3427 (OH), 2923 (CH), 1255 (SO$_3$); $\delta_H$(500 MHz, CD$_3$OH) 3.29–3.31 (1H, m, 2-H), 3.46–3.89 (4H, m, 4'-H, 5'-H, 6-Ha, 6-Hb), 4.14 (1H, dd, J 10.08, 4.5, 6'-Ha), 4.24 (1H, dd, J 10.7, 7.9, 6'-Hb), 4.36 (1H, d, J 7.4, 1'-H), 4.65 (1H, d, J 9.8, 1-H), 7.25–7.32 (3H, m, Ph), 7.55–7.57 (2H, m, Ph); $\delta_C$(125.78 MHz, CD$_3$OD) 62.18 and 67.96 (2 CH$_2$), 69.95, 72.29, 73.33, 74.56, 74.76, 77.84, 80.38 and 81.33 (8 CH), 86.74 (1-C), 105.23 (1'-C), 128.52 (CH), 129.92 (2 CH), 133.03 (2 CH), 134.72 (C); m/z (ES$^-$) 513 [(M-H)$^-$, 100%].

Phenyl 1-deoxy-4-O-(3'-O-sulfo-β-D-galatopyranosyl)-1-thio-β-D-glucopyranoside, sodium salt 15 and Phenyl 1-deoxy-4-O-(3',6',-di-O-sulfo-β-D-galactopyranosyl)-1-thio-β-D-glucopyranoside, disodium salt 16:

8 (199 mg, 458 μmol) was stirred in refluxing MeOH (4 ml), with Bu$_2$SnO (116.5 mg, 458 μmol) for 2 hours under nitrogen. The solvent was reduced in vacuo and the dry dibutylstannylene complex was treated with Me$_3$N.SO$_3$ (132 mg, 920 μmol) in dioxane (4 ml) at room temperature for 30 hours. The reaction mixture was diluted with MeOH (3 ml), filtered and reduced in vacuo. The residue was dissolved in MeOH (3 ml) and loaded onto a cation exchange resin column (AG50W-X8, Na$^+$, 1×4 cm). The products were eluted with MeOH, the eluant concentrated in vacuo and chromatographed (MeOH/CHCl$_3$/H$_2$O 5:8:1) to give 15 (187.2 mg, 76%) and 16 (29.1 mg, 10%) as white solids: 15 $[\alpha]^{24}{}_D$ –26.2 (c 4.8 in MeOH); m.p. 215° C. (dec.); Rf 0.23 (MeOH/CHCl$_3$/H$_2$O 5:8:1); $\nu_{max}$ (KBr)/cm$^{-1}$ 3402 (OH), 2920, 2880 (CH), 1584 (C=C), 1250 (SO$_3{}^-$); $\delta_H$(500 MHz; CD$_3$OD) 3.28 (1H, dd, J 9.7, 8.4, 2-H), 3.43–3.46 (1H, m, 5-H), 3.55 (1H, dd, J 8.7, 8.7, 3-H), 3.59 (1H, dd, J 9.6, 9.6, 4-H), 3.63 (1H, m, 5'-H), 3.68–3.73 (2H, m, 2'-H, 6'-Ha), 3.77 (1H, dd, J 11.5, 7.5, 6'-Hb), 3.85 (1H, dd, J 12.3, 4.1, 6-Ha), 3.91 (1H, dd, J 12.3, 2.5, 6-Hb), 4.21–4.25 (2H, m, 3'-H, 4'-H), 4.48 (1H, d, J 7.8, 1'-H), 4.62 (1H, d, J 9.8, 1-H), 7.24–7.32 (3H, m, Ph), 7.54–7.56 (2H, m, Ph); $\delta_C$(125.78 MHz, CD$_3$OD) 61.98 and 62.43 (2 CH$_2$), 68.55, 70.87, 73.41, 76.75 and 77.93 (5 CH), 80.51 (2 CH), 81.75 (CH), 89.12 (1-C), 104.82 (1'-C), 104.82 (1'-C), 128.44 (CH), 129.88 (2 CH), 133.01 (2 CH), 134.92 (C); m/z (FAB$^-$) Found: 513.0738 [(M-Na)$^+$], C$_{18}$H$_{25}$O$_{13}$S$_2{}^-$ requires 513.0737; 16: $[\alpha]^{24}{}_D$ –29.9 (c 1.5 in MeOH); m.p. 194° C. (dec.); Rf 0.13 (MeOH/CHCl$_3$/H$_2$O 5:8:1); $\nu_{max}$ (KBr) 3431 (OH). 2928 (CH), 1251 (SO$_3$): $\delta_H$(500 MHz; CD$_3$OD) 3.33–3.35 (1H, m, 2-H), 3.51–3.54 (1H, m, 5-H), 3.61 (1H, dd, J 8.9, 8.9, 4-H), 3.65 (1H, dd, J 8.7, 8.7, 3-H), 3.75 (1H, dd, J 7.9, 9.6, 2'-H), 3.87 (1H, dd, J 4.4, 12.3, 6-Ha), 3.95 (1H, dd, J 2.5, 12.4, 6-Hb), 3.96–3.99 (1H, m, 5'-H), 4.16 (1H, dd, J 3.7, 10.8, 6'-Ha), 4.27 (1H, d, J 3.3, 4'-H), 4.29–4.36 (2H, m, 3'-H, 6'-Hb), 4.50 (1H, d, J 7.8, 1'-H), 4.72 (1H, d, J 9.8, 1-H), 7.28–7.36 (3H, m, Ph), 7.59–7.61 (2H, m, Ph); $\delta_C$(125.78 MHz; CD$_3$OD) 62.07 (6-C), 68.29 (6'-C, CH), 70.54, 73.20, 74.47, 77.81, 80.35, 81.31, 81.59 (7 CH), 88.35 (1-C), 105.02 (1'-C), 128.64 (CH, Ph), 129.98 (2 CH, Ph). 133.12 (2 CH, Ph), 134.46 (C, Ph): m/z (FAB$^-$) Found: 615.0117 [(M-Na)$^-$], C$_{18}$H$_{24}$O$_{16}$SNa$^-$ requires 615.0124.

Phenyl 1-deoxy-4-O-(6'-O-sulfo-β-D-galactopyranosly)-1-thio-β-D-glucopyranoside 14, Phenyl 1-deoxy-4-O-(β-D-galactopyranosyl)-6-O-sulfo-1-thio-β-D-glucopyranoside 17 and Phenyl 1-deoxy-6-O-sulfo-4-O-(6'-O-sulfo-β-D-galactopyranosyl)-1-thio-β-D-glucopyranoside 18:

A solution of 8 (50 mg, 115 μmol) in DMF (1 ml) was treated with Me$_3$N.SO$_3$ (33 mg, 230 μmol) and stirred at room temperature for 4 days. The reaction mixture was concentrated in vacuo and chromatographed (MeOH/CHCl$_3$/H$_2$O 5:8:1) to give the unreacted starting material (6.3 mg, 13%) and 14 (10.2 mg, 17%), 17 (5.3 mg, 9%), 18 (10.6 mg, 15%); 17: Rf 0.22 (MeOH/CHCl$_3$/H$_2$O 4:5:1); $\delta_H$(500 MHz; CD$_3$OD) 3.26 (1H, dd, J 9.7, 8.8, 2-H), 3.50–3.51 (2H, m, 2'-H, 4'-H), 3.53 (1H, dd, J 8.8, 8.8, 3-H) 3.60 (1H, dd, J 9.1, 9.1, 4-H), 3.60–3.62 (1H, m, 5'-H), 3.66–3.69 (1H, m, 5-H), 3.69 (1H, dd, J 11.6, 4.8, 6'-Ha), 3.76 (1H, dd, J 11.5, 7.4, 6'-Hb), 3.81 (1H, d, J 1.4, 3'-H), 4.30 (1H, dd, J 11.0, 4.3, 6-Ha), 4.35 (1H, dd, J 11.0, 1.9, 6-Hb), 4.48 (1H, d, J 7.7, 1'-H), 4.58 (1H, d, J 9.8, 1-H), 7.23, 7.32 (3H, m, Ph), 7.55–7.59 (2H, m, Ph); $\delta_C$(125.78 MHz, CD$_3$OD) 62.49 and 67.51 (2 CH$_2$), 70.43, 72.75, 73.32, 74.82, 77.02, 77.88, 78.26 and 79.62 (8 CH), 88.99 (1-C), 104.65 (1'-C), 128.52 (CH), 129.89 (2 CH), 133.42 (2 CH), 134.59 (C); m/z (ES$^-$) 513 [(M-H)$^-$]; 18: m.p. 180° C. (dec.); Rf 0.16 (MeOH/CHCl$_3$/CHCl$_3$/H$_2$O 4:5:1); $\nu_{max}$ (KBr)/cm$^{-1}$ 3435 (OH), 2922 (CH), 1251 (SO$_3$); $\delta_H$(500 MHz; CD$_3$OD) 3.28–3.31 (1H, m, 2-H), 3.52–3.57 (4H, m, 2'-H, 4'-H, 3-H, 4-H), 3.70–3.73 (1H, m, 5-H), 3.86 (1H, d, J 1.3, 3'-H), 3.88–3.90 (1H, m, 5'-H), 4.14 (1H, dd, J 10.7, 4.5, 6'-Ha), 4.24 (1H, dd, J 10.7, 8.0, 6'-Hb), 4.28 (1H, dd, J 11.0, 4.8, 6-Ha), 4.36 (1H, dd, J 11.0, 1.8, 6-Hb), 4.45 (1H, d, J 7.7, 1'-H), 4.62 (1H, d, J 9.8, 1-H), 7.24–7.32 (3H, m, Ph), 7.57–7.59 (2H, m, Ph); $\delta_C$(125.78 MHz, CD$_3$OD) 67.70 and 67.95 (2 CH$_2$), 69.99, 72.51, 73.17, 74.53, 74.75, 77.82, 78.16 and 81.16 (8 CH). 88.59 (1-C), 105.14 (1'-C), 128.55 (CH), 129.94 (2 CH), 133.30 (2 CH), 134.50 (C); m/z (ES$^-$) 615 [(MNa-2H)$^-$, 54%], 296 [(M-2H)$^{2-}$, 100].

Phenyl 2-acetamido-3,4,6-tri-O-acetyl-1,2-di-deoxy-1-thio-β-D-glucopyranoside 19:

To a solution of chloro 2-acetamido-3,4,6-tri-O-acetyl-2-deoxy-α-D-glucopyranoside (844 mg. 2.31 mmol) in CH$_3$CN (10 ml) was added thiophenyl (280 μl, 2.72 mmol) and Et$_3$N (633 μl, 4.54 mmol). The reaction mixture was stirred 1.5 hours at room temperature, filtered, concentrated in vacuo and chromatographed (AcOEt) leading to 19 as a white solid (968 mg, 95%): $[\alpha]^{24}{}_D$ –20.4 (c 3.3 in CHCl$_3$); m.p. 199° C.; Rf 0.35 (AcOEt); $\nu_{max}$ (CDCl$_3$)/cm$^{-1}$ 3287 (NH), 2960, 2880 (CH), 1747 (CH$_3$C=O), 1687 (NHC=O), 1514 (NH), 1239 (C-O); $\delta_H$(200 MHz; CDCl$_3$) 1.98, 2.00, 2.02, and 2.07 (12H, 4×s, 4×Ac), 3.73 (1H, ddd, J 3.0, 5.0, 10.5, 5-H), 4.04 (1H, ddd, J 10.0, 10.0, 10.0, 2-H), 4.17–4.21 (2H, m, 6-Ha, 6-Hb), 4.87 (1H, d, J 10.4, 1-H), 5.05 (1H, dd, J 9.7, 9.7, 4-H), 5.24 (1H, dd, J 9.7, 9.7, 3-H), 5.81 (1H, d, J 9.3, NH), 7.27–7.31 (3H, m, Ph), 7.47–7.52 (2H, m, Ph); $\delta_C$(50 MHz; CDCl$_3$) 20.39 (CH$_3$), 20.55 (2 CH$_3$), 23.12 (CH$_3$), 53.15 (2-C), 62.36 (6-C), 68.50, 73.66 and 75.61 (3 CH), 86.53 (1-C), 128.10 (CH, Ph), 129.03 (2 CH, Ph), 132.45 (2 CH, Ph), 132.76 (C, Ph), 169.61, 170.45, 170.88 and 171.21 (4 CO); m/z (CI) Found: 440.1379 (MH$^+$), C$_{20}$H$_{26}$O$_8$NS$^+$ requires 440.1379.

Phenyl 2-acetamido-1,2-di-deoxy-1-thio-β-D-glucopyranoside 20:

A solution of 19 (102.5 mg, 233 μmol) in MeOH (2 ml) was stirred with a 0.6M sodium methoxide solution (149 μl, 89 μmol) at room temperature for 0.5 hours. The reaction mixture was diluted with MeOH (5 ml) and neutralized with Amberlite-IR (H$^+$) resin. The resin was removed by filtration and washed with MeOH. The filtrate and washings were reduced in vacuo leading to 20 as a white solid (72 mg, 99%): $[\alpha]^{23}{}_D$ +6.6 (c 0.8 in MeOH); m.p. 222° C.; Rf 0.50 (MeOH/CHCl$_3$/H$_2$O 4:5:1); $\nu_{max}$ (KBr)/cm$^{-1}$ 3360, 3287 (OH, NH), 2940, 2880 (CH), 1651 (C=O), 1541 (NH); $\delta_H$(500 MHz; CD$_3$OD) 2.02 (3H, s, Ac), 3.33–3.40 (2H, m, 4-H, 5-H), 3.49 (1H, dd, J 8.3, 9.8. 3-H), 3.71 (1H, dd, J 5.6, 12.1, 6-Ha), 3.79 (1H, dd, J 10.1, 10.1, 2-H), 3.90 (1H, dd, J 2.2, 12.2, 6-Hb), 4.81 (1H, d, J 10.4, 1-H), 7.26–7.33 (3H, m, Ph), 7.51–7.53 (2H, m, Ph); $\delta_C$(125.78 MHz; CD$_3$OD) 22.96 (CH$_3$), 56.28 (2-C), 62.86 (6-C), 71.83, 77.43 and 82.12 (3 CH), 88.38 (1-C), 128.17 (CH, Ph), 129.90 (2 CH, Ph), 132.11 (2 CH, Ph), 135.93 (C, Ph), 173.54 (CO); m/z (CI) Found: 314.1062 (MH$^+$), C$_{14}$H$_{20}$O$_5$NS$^+$ requires 314.1062.

Phenyl 2-acetamido-1,2-di-deoxy-4-O-(β-D-galactopyranosyl)-1-thio-β-D-glucopyranoside 21:

20 (12.5 mg, 40 μmol) was sonicated with 50 mM sodium cacodylate buffer (pH 7.4, 1 ml) containing MnCl$_2$ (2 mM), and NaN$_3$ (6 mM) for 15 min. To the white suspension were added BSA (0.9 mg), CIAP (7 U), UDP-glucose (29.9 mg, 48 μmol). UDP-galactose 4-epimerase (4 U) and β-galactosyltransferase (1.07 U). The reaction mixture was incubated at 37° C., after 17 hours the clear solution was reduced in vacuo and the residue chromatographed twice (MeOH/CHCl$_3$/H$_2$O 4:5:1, then MeOH/CHCl₃ 1:4) affording 21 as a white solid (11.3 mg, 60%): $[\alpha]^{23}_D$+8.3 (c 0.9 in H₂O); m.p. 228° C.; Rf 0.35 (MeOH/CHCl₃/H₂O 4:5:1); $\nu_{max}$ (KBr) /cm⁻¹ 3409, 3300 (OH, NH), 2940, 2880 (CH), 1646 (C=O), 1548 (NH); $\delta_H$(500 MHz; CD₃OD) 2.01 (3H, s, Ac), 3.46–3.47 (1H, m, 5-H). H), 3.50 (1H, dd, J 3.2, 9.7, 3'-H), 3.55 (1H, dd, J 7.5, 9.7, 2'-H), 3.60 (1H, dd, J 4.6, 7.5, 5'-H), 3.66–3.68 (2H, m, 3-H, 4-H), 3.70 (1H, dd, J 4.5, 11.5, 6'-Ha), 3.78 (1H, dd, J 7.5, 11.5, 6'-Hb), 3.83 (1H, d, J 3.2, 4'-H), 3.85–3.89 (2H, m, 2-H, 6-Ha), 3.94 (1H, dd, J 2.5, 12.3, 6-Hb), 4.41 (1H, d, J 7.5, 1'-H), 4.81 (1H, d, J 10.5, 1-H), 7.27–7.33 (3H, m, Ph), 7.50–7.52 (2H, m, Ph); $\delta_C$(125.78 MHz; CD₃OD) 22.92 (CH₃), 55.69 (2-C), 62.00 and 62.54 (2 CH₂), 70.34, 72.60, 74.83, 75.59, 77.17, 80.52 and 80.67 (7 CH), 88.49 (1-C), 105.03 (1'-C), 128.31 (CH, Ph), 129.93 (2 CH, Ph), 132.32 (2 CH, Ph), 135.74 (C, Ph), 173.37 (CO); m/z (DCI) 476 (MH⁺, 5%), 366 [(M-SPh)⁺, 36], 204 [(M-271)⁺, 100].

Phenyl 2-acetamido-3,6-di-O-acetyl-4-O-(2',6'-di-O-acetyl-β-D-galactopyranosyl)-1,2-di-deoxy-1-thio-β-D-glucopyranoside 22:

A solution of 21 in pyridine/Ac₂O 2:1 (300 μl) was stirred at room temperature for 45 h, reduced in vacuo and chromatographed (MeOH/CHCl₃ 1:9) leading to 22 (1.2 mg, 28%): Rf 0.22 (MeOH/CHCl₃ 1:9); $\delta_H$(500 MHz; CDCDl₃) 1.98, 2.07, 2.10, 2.11 and 2.13 (15H, 5×s, 5×Ac), 3.60–3.66 (2H, m, 3'-H, 5'-H), 3.67 (1H, dd, J 2.2, 6.2, 5-H), 3.73 (1H, dd, J 9.1, 9.1, 4-H), 3.85 (1H, d, J 3.4, 4'-H), 4.10–4.18 (2H, m, 2-H, 6-Ha), 4.23 (1H, dd, J 6.3, 11.4, 6'-H), 4.37 (1H, dd, J 6.4, 11.7, 6'-Hb), 4.38 (1H, d, J 7.7, 1'-H), 4.53 (1H, dd, J 2.1, 11.7, 6-Hb), 4.70 (1H, d, J 10.4, 1-H), 4.86 (1H, dd, J 7.9, 9.7, 2'-H), 5.08 (1H, dd, J 8.7, 9.9, 3-H), 5.68 (1H, d, J 9.5, NH), 7.28–7.31 (3H, m, Ph), 7.47–7.49 (2H, m, Ph); m/z (DCI) 664 (MH⁺, 58%), 534 [(M-SPh)⁺, 95%], 168 [(M-475)⁺, 100].

Phenyl 2-acetamido-1,2-di-deoxy-4-O-(3'-O-sulfo-β-D-galactopyranosyl)-1-thio-β-D-glucopyranoside, sodium salt 23:

21 (43 mg, 90 μmol) was treated as described for the synthesis of 15 using THF (43 h) instead of dioxane to give 23 as a white solid (43.2 mg, 83%): $[\alpha]^{24}_D$-13 (c 2.9 in MeOH); m.p. 205° C. (dec.); Rf 0.10 (MeOH/CHCl₃/H₂O 5:10:1); $\nu_{max}$ (KBr)/cm⁻¹ 3403 (OH, NH), 2940, 2880 (CH), 1557 (Ph), 1651 (C=O), 1557 (NH), 1250 (SO₃⁻); $\delta_H$(500 MHz; CD₃OD) 2.00 (3H, s, Ac), 3.44 (1H, ddd, J 2.6, 4.0, 9.1, 5-H), 3.62–3.66 (3H, m, 3-H, 4-H, 5'-H), 3.66–3.73 (2H, m, 2'-H, 6'-Ha), 3.76 (1H, dd, J 7.5, 11.5, 6'-Hb), 3.84–3.88 (2H, m, 2-H, 6-Ha), 3.92 (1H, dd, J 2.5, 12.3, 6-Hb), 4.22 (1H, d, J 3.2, 4'-H), 4.25 (1H, dd, J 3.2, 9.7, 3'-H), 4.51 (1H, d, J 7.8, 1'-H), 4.79 (1H, d, J 10.5, 1-H), 7.22–7.30 (3H, m, Ph), 7.47–7.89 (2H, m, PH); $\delta_C$(50 MHz; CD₃OD) 22.25 (CH₃), 55.01 (2-C), 61.91 and 61.38 (2 CH₂), 68.06, 70.35, 75.12 and 76.18 (4 CH), 80.05 (2 CH), 81.13 (3'-C), 87.86 (1-C), 104.25 (1'-C), 127.94 (CH, PH), 129.62 (2 CH, Ph), 131.87 (2 CH, Ph), 135.32 (C, Ph), 173.33 (CO); m/z (FAB⁻) Found: 554.0999 [(M-Na)⁺], $C_{20}H_{28}O_{13}S_2^-$ requires 554.1002.

Methyl 3-O-sulfo-β-D-galactopyranoside, sodium salt 25:

Methyl β-D-galactopyranoside 24 (100 mg, 515 μmol) was treated as described for the synthesis of 15 using THF (15 h) instead of dioxane and the product converted to its sodium salt by using MeOH/CHCl₃ 1:1 as solvent. Chromatography (MeOH/CHCl₃/H₂O 4:5:1) gave 25 as a white gum (142 mg, 93%): $[\alpha]^{23}_D$+8.3 (c 3.6 in MeOH); Rf 0.16 (MeOH/CHCl₃/H₂O 4:5:1); $\nu_{max}$ (KBr)/cm⁻¹ 3436 (OH), 2947 (CH), 1251 (SO₃); $\delta_H$(500 MHz; CD₃OD) 3.53 (3H, s, OMe), 3.56 (1H, dd, J 6.09, 6.09, 5-H), 3.67 (1H, dd, J 7.9, 8.8, 2-H), 3.74 (1H, d, J 5.5, 6-Hb), 3.75 (1H, d, J 6.6, 6-Ha), 4.22–4.25 (3H, m, 1-H, 3-H), 4-H); $\delta_C$ (50 MHz, CD₃OD) 55.80 (CH₃), 60.93 (CH₂), 67.16, 69.30, 74.91 and 80.58 (4 CH), 104.37 (1-C); m/z (FAB⁻) Found: 273.0276 [(M-Na)⁻], $C_7H_{13}O_9S^-$ requires 273.0280.

Methyl 2,4,6-tri-O-acetyl-3-O-sulfo-β-D-galactopyranoside, sodium salt 26:

A solution of 25 (17.4 mg, 59 μmol) in Ac₂O/pyridine 1:2 (450 μl) was stirred for 2 hours and reduced in vacuo. The residue was dissolved in toluene (2 ml) and reduced again to give a white solid (24 mg, 97%); Rf 0.47 (MeOH/CHCl₃/H₂O 4:5:1); $\nu_{max}$ (KBr)/cm⁻¹ 2925 (CH), 1737 (C-O), 1263 (SO₃, C-O); $\delta_H$(500 MHz; CDCl₃) 1.95, 2.00 and 2.11 (9H, 3×s, 3×Ac), 3.51 (3H, s, OMe), 3.84 (1H, dd, J 11.1, 11.1, 5-H), 4.31 (1H, d, J 10.0, 6-Ha), 4.71 (1H, d, J 8.1, 1-H), 4.83 (1H, dd, J 3.2, 10.5, 3-H), 5.01 (1H, d, J 11.5, 6-Hb), 5.14 (1H, dd, J 8.3, 10.2, 2-H), 6.04 (1H, broad s, 4-H); $\delta_C$(125.78 MHz, CDCl₃) 14.17, 20.26, 21.05 and 21.13 (4 CH₃), 56.42 (6-C), 69.57, 70.01, 70.36 and 75.08 (4 CH), 101.04 (1-C), 168.28, 169.82 and 173.09 (3 CO); m/z (ES⁻) 399 [(M-Na)⁻, 100%].

3-O-sulfo-β-D-galactosylceramide, sodium salt 3 and 3,6-di-O-sulfo-β-D-galactosylceramide, disodium salt 28:

Galactosylceramide 27 (41.8 mg, 51 μmol) was sulfated as described for 25 using 1.5 equivalent of Bu₂SnO then stirring with Me₃N.SO₃ at room temperature for 4 hours. The residue was chromatographed twice (MeOH/CHCl₃ 1:4 then MeOH/CHCl₃/H₂O 5:10:1) to give 3 as a white solid (45.2 mg, 97%) and a trace of 28; 3: $[\alpha]^{23}_D$+2.6 (c 1.0 in MeOH); m.p. 184° C. (dec.); Rf 0.35 (MeOH/CHCl₃/H₂O 5:10:1); $\nu_{max}$ (KBr)/cm⁻¹ 3435 (OH, NH), 2920, 2851 (CH), 1635 (C=O), 1556 (NH), 1250 (SO₃); $\delta_H$(500 MHz; CD₃OD/CDCl₃ 1:1) 0.85 (6H, t, J 6.9, 2×CH₃), 1.20–1.35 (54H, m, 27×CH₂), 1.54–1.56 (2H, m, NHCOCH₂CH₂). 1.97–2.00 (6H, m, 3×CH=CHCH₂), 2.13–2.16 (2H, t, J 7.7, NHCOCH₂), 3.55 (1H, dd, J 5.9, 5.9, 5-H), 3.61 (1H, dd, J 3.0, 10.3, OCHaHbCNH), 3.70–3.80 (3H, m, 6-Ha, 6-Hb, 2-H), 3.95–3.98 (1H, m, CHNH), 4.07 (1H, dd, J 7.7, 7.7, CHOHCNH), 4.14 (1H, dd, J 4.7, 10.3, OCHaHbCNH), 4.24–4.27 (2H, m, 3-H, 4-H), 4.32 (1H, d, J 7.7, 1-H). 5.30 (2H, t, J 4.7, cis CH=CH), 5.41 (1H, dd, J 7.6, 15.3, CHOHCHa=CHb), 5.66 (1H, dt, J 7.2, 15.3, CHOHCHa=CHb), 7.67 (1H, d, J 9.2, NH); $\delta_C$(125.78 MHz; CD₃OD/CDCl₃ 1:1) 14.33 (2 CH₃), 23.20 (2 CH₂), 26.61 (CH₂), 27.68 (2 CH₂), 29.87, 29.94 and 30.29 (23 CH₂), 32.49 (2 CH₂), 32.98 (CH₂), 37.02 (CH₂), 53.99 (CH), 61.89 (CH₂), 68.02 (CH), 69.50 (CH₂), 70.23, 72.39, 75.41 and 80.94 (4 CH), 103.98 (1-C), 130.04 (C=), 130.37 (C=C), 134.87 (C=), 175.45 (CO); m/z (FAB⁻) Found: 888.6240 [(M-Na)⁻], $C_{48}H_{90}NO_{11}S^-$ requires 888.6235; 28: Rf 0.18 (MeOH/CHCl₃/H₂O 5:10:1); $\nu_{max}$ (KBr)/cm⁻¹ 3435 (OH,NH), 2921, 2851 (CH), 1630 (C=O), 1560 (NH), 1252 (SO₃); $\delta_H$(500 MHz; CD₃OD/CDCl₃ 1:1) 0.85 (6H, t, J 6.9, 2×CH₃), 1.23–1.32 (54H, m, 27×CH₂), 1.53–1.56 (2H, m, CH₂CH₂CONH), 1.97–2.00 (6H, m, 3×CH₂CH=CH), 2.14 (2H, t, J 7.7, CH₂CONH), 3.56 (1H, dd, J 2.9, 10.3, CHaHbCNH), 3.73 (1H, dd, J 7.9, 9.5, 2-H) 3.81 (1H, dd, J 6.4, 6.4, 5-H), 3.96–3.98 (1H, m, CHNH), 4.06 (1H, dd, J 7.8, CHOHCNH), 4.13–4.23 (3H, m, CHaHbCNH, 6-Ha, 6-Hb), 4.25–4.31 (2H, m, 3-H, 4-H), 4.33 (1H, d, J 7.7, 1-H), 5.30 (2H, t, J 4.7, cis CH=CH), 5.41 (1H, dd, J 7.6, 15.3, CHOHCHa=CHb), 5.66 (1H, dt, J 6.7, 15.3, CHOHCHa=CHb), 7.74 (1H, d, J 8.0, NH); m/z (FAB⁻)

Found: 990.5659 [(M-Na)⁻] and 968.5781 [(MH-2Na)⁻], $C_{48}H_{89}NO_{14}S_2Na^-$ requires 990.5622 and $C_{48}H_{90}NO_{14}S_2^-$ requires 968.5803.

Benzyl 4-O-(4'-,6'-O-benzylidene-2'-O-sulfo-α-D-glucopyranosyl)-β-D-glucopyranoside 30:

29 (54 mg, 104 µmol) was sulfated as described for 15 and chromatographed using CH₂Cl₂:MeOH (8:2) giving 30 as a white gummy solid (54 mg, 87%): [α]²³_D+26.0 (c 1.0 in MeOH); Rf 0.40 (CH₂Cl₂/MeOH 8:2); δ_H(500 MHz; CD₃OD) 3.34–3.35 (1H, m, 2-H), 3.40–3.43 (1H, m, 6-H), 3.59 (1H, t, J 9.5, 4'-H), 3.69–3.79 (4H, m, 3-H, 6-Hb, 6'-H), 3.86–3.89 (1H, m, 5'-H), 3.90–3.94 (1H, m, 5-H), 3.97 (1H, t, J 9.6, 3'-H), 4.26 (1H, dd, J 10.1, 4.8, 4-H), 4.33 (1H, dd, J 9.6, 4.0, 2'-H), 4.41 (1H, d, J 7.9, 1-H), 4.79 (2H, dd, J 12.7, 11.8, PhCH₂), 5.59 (1H, s, PhCH), 5.76 (1H, d, J 4.01, 1'-H), 7.25–7.51 (10H, m, PhCH₂, PhCH); δ_C(125.78 MHz; CD₃OD) 62.63, 64.43, 69.69, 70.00, 71.75, 74.80, 76.30, 77.76, 78.20, 79.55, 82.35, (2-C, 3-C, 4-C, 5-C, 6-C, 2'-C, 3'-C, 4'-C, 5'-C, 6'-C, PhCH₂), 98.96, 102.95, 103.06, (1-C, 1'-C, PhCH), 127.51, 128.68, 129.02, 129.17, 129.27, 129.92, 139.04 (PhCH₂, PhCH); m/z (ES⁻) 599 [(M-H)⁻, 100%].

Tert-butyl [allyl 4-O-(4',6'-O-benzylidene-2'-O-sulfo-α-D-glucopyranosyl)-β-D-glucopyranosid]uronate 32:

31 (55 mg, 100 µmol) was sulfonated as described for 15 to give 32 as a colourless gum (34 mg, 54%): Rf 0.33 (CH₂Cl₂/MeOH 8:2); δ_H(500 MHz; CD₃OD) 1.52 (9 H, s, C(CH₃)₃), 3.27 (1H, dd, J 7.9, 9.3, 2-H), 3.54 (1H, t, J 9.3, 4'-H), 3.69–3.74 (3H, m, 5'-H, 6'-H), 3.77 (1H, dd, J 8.9, 9.0, 3-H), 3.81 (1H, d, J 9.6, 5-H), 3.89 (1H, t, J 9.5, 3'-H), 3.95 (1H, dd, J 8.9, 9.3, 4-H), 4.13–4.17 (1H, m, OCH₂), 4.24–4.32 (2 H, m, 2'-H, OCH₂), 4.40 (1H, d, J 7.9, 1-H), 5.15–5.17 (1H, m, CH=CH₂), 5.30–5.34 (1H, m, CH=CH₂), 5.56 (1H, s, PhCH), 5.89 (1H, d, J 4.0, 1'-H), 5.91–5.99 (1 H, m, CH=CH₂), 7.31–7.46 (5 H, m, Ph); δ_C(125.78 MHz; CD₃OD) 28.54 [C(CH₃)₃], 69.50 and 71.47 (6'-C, OCH₂), 63.90, 69.82, 74.35, 76.63, 77.06, 77.70, 79.31 and 82.27 (2-C, 3-C, 4-C, 5-C, 2'-C, 3'-C, 4'-C, 5'-C), 83.73 (CMe₃), 98.09, 103.01 and 103.76 (1-C, 1'-C, PhCH), 117.69 (OCH₂CH=CH₂), 127.54, 128.99 and 129.91 (5 CH, Ph), 135.47 (OCH₂CH=CH₂), 139.06 (C, Ph), 169.16 (C=O); m/z (FAB⁻) Found: 619.1708 [(M-H)⁻], $C_{26}H_{35}O_{15}S^-$ requires 619.1697.

Allyl 4-O-(4',6'-O-benzylidene-2'-O-sulfo-α-D-glucopyranosyl)-6-O-tert-butyldimethylsilyl-β-D-glucopyranoside 34:

33 (50 mg, 86 µmol) was sulfated as described for 15 and stirred with Me₃N.SO₃ for 93 hours at room temperature. Chromatography (CH₂Cl₂/MeOH 8:2) gave 34 as a colourless gum (32 mg, 52%): Rf 0.44 (CH₂Cl₂/MeOH 8:2); [α]²⁵_D+32.23 (c 1.03 in MeOH); δ_H(500 MHz; CD₃OD) 0.11 and 0.12 (6 H, 2s, SiMe₂), 0.92 (9 H, s, tBu), 3.23 (1H, dd, J 8.1, 8.6, 2-H), 3.35–3.38 (1H, m, 5-H), 3.58 (1H, t, J 9.5, 4'-H), 3.72–3.77 (3H, m, 3-H, 4-H, 6'-Ha), 3.86–3.98 (4H, m, 3'-H, 5'-H, 6'-H), 4.11–4.16 (1H, m, OCH₂), 4.23 (1H, dd, J 4.8, 10.1, 6'-Hb), 4.29 (1H, dd, J 4.0, 9.6, 2'-H), 4.30–4.33 (1H, m, OCH₂), 4.33 (1H, dd, J 7.9, 1-H), 5.14–5.33 (2H, m, CH=CH₂), 5.59 (1H, s, PhCH), 5.83 (1H, d, J 4.0, 1'-H), 5.92–5.99 (1H, m, CH=CH₂), 7.32–7.50 (5H, m, Ph); δ_C(125.78 MHz; CD₃OD) -4.89 and -4.81 (SiMe₂), 19.38 (CMe₃), 26.58 (CMe₃), 63.81, 69.73 and 70.89 (6-C, 6'-C, OCH₂-CH=CH₂), 64.48, 69.89, 74.73, 76.39, 76.84, 78.38, 79.52 and 82.44 (2-C, 3-C, 4-C, 5-C, 2'-C, 3'-C, 5'-C), 98.78, 102.83 and 103.02 (1-C, 1'-C, PhCH), 117.52 (OCH₂CH=CH₂), 127.57, 128.99 and 129.95 (5 CH, Ph), 135.69 (OCH₂CH=CH₂), 139.04 (C, Ph); m/z (FAB⁻) Found: 663.2149 [(M-H)⁻], $C_{28}H_{42}O_{14}SiS^-$ requires 663.2143.

As mentioned above, sulfated saccharides and glycoconjugates, in which one or several of the hydroxyl or amino groups of the sugar are esterified as sulfate esters are abundant in biological systems. Examples of such structures include sulfate glycolipids (for example 3), sulfated glycosaminoglycans, such as heparin, heparan sulfate, chondroitin sulfate, dermatan sulfate or keratan sulfate (see, for example, Lander, A. D., Chemistry & Biology, 1, 73–78, 1994), and some blood group antigens, such as sulfated Lewis^x and Lewis^a antigens, which may be either attached to proteins or lipids (see, for example, the first-mentioned papers by Yuen et al). It is interesting to note that the sulfated Lewis antigens may have similar biological activity to those Lewis antigens containing a sialic acid at the same position of the sugar.

These sulfated saccharides have important roles in diverse biological processes, such as cell adhesion, cell proliferation, angiogenesis, cell differentiation, cell invasion or cell attachment (see, for example, Lander, loc cit). Such processes have physiological significance in a diverse range of scientific and clinical areas, such as blood coagulation, cancer, atherosclerosis, inflammation, wound healing and degenerative nervous system diseases. Compounds that selectively mimic or inhibit these processes may therefore have considerable therapeutic importance. Such compounds may either be partial structures of sulfated oligosaccharides or analogues of such structures. One of the challenges in this area is the chemical synthesis of these complex molecules. Although advances have been made in this area (see, for example, Lubineau, et al, loc cit, and Nicolaou, et al, loc cit), the syntheses are long and low yielding due to the need for complex protection group strategies.

The present methodology of regioselective sulfation has the advantage that it requires little protection and therefore substantially reduces the number of synthetic steps. For example, the classical synthesis of compound 23 from 21 requires five steps, while the present methodology converts 21 to 23 in one high-yielding step. Since it requires few protecting groups it may be used in combination with enzymatic methodologies as demonstrated in above Scheme 6: 21 is first made enzymatically from 20, then regioselectively sulfated to 23. It has been shown that 23 is a substrate for a fucosyltransferase, which then gives the sulfo-Lewis^x antigen structure (see, for example, Chandrasekaran, et al, loc cit).

The present sulfation methodology does not only give access to 3-sulfated galactosides, but may also be used to sulfate other positions, such as illustrated in above Scheme 4 (8 to 14) and above Table 1 (29 to 30). It may be used in the presence of a number of functional groups, such as acetals (29), allylic alcohols (27), silyl ethers (33), amides (27) and esters (31). So far it has been applied particularly to saccharides and glycolipids, but it is also applicable to glycopeptide synthesis, given its tolerance for functional groups.

The present methodology may be used to make natural compounds (such as 3) and it may be applied to the synthesis of useful novel compounds (such as 14, 15, 16, 23, 25, 30, 32 and 34).

We claim:

1. An organic molecule represented by the following formula:

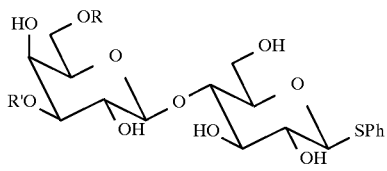

wherein R is H or SO$_3$H, and R' is H or SO$_3$H.

2. An organic molecule represented by the following formula:

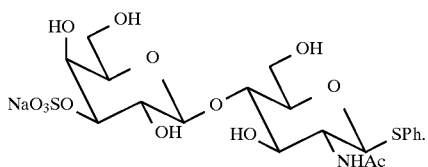

3. An organic molecule represented by the following formula:

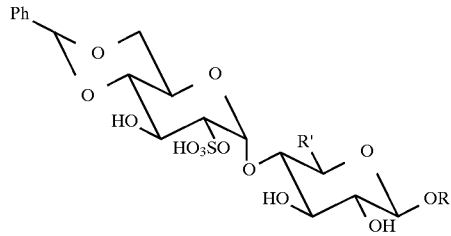

wherein when R is Bn, R' is CH$_2$CH; and when R is alkyl, R' is CO$_2$tert-Bu or CH$_2$OSitert-BuMe$_2$.

4. An organic molecule as claimed in claims 1, 2, or 3 wherein it is conjugated to a larger molecule.

* * * * *